United States Patent [19]

Mortara

[11] Patent Number: 5,490,515
[45] Date of Patent: *Feb. 13, 1996

[54] FILTER APPARATUS AND METHOD FOR REDUCING SIGNAL NOISE USING A PLURALITY OF SIGNALS OBTAINED FROM A SIGNAL SOURCE

[75] Inventor: avid W. Mortara, River Hills, Wis.

[73] Assignee: Mortara Instrument, Inc., Milwaukee, Wis.

[*] Notice: The portion of this term of this patent subsequent to Jun. 6, 2012.

[21] Appl. No.: 297,496

[22] Filed: Aug. 29, 1994

Related U.S. Application Data

[63] Continuation of Ser. No. 71,337, Jun. 2, 1993, Pat. No. 5,421,342, which is a continuation of Ser. No. 643,719, Jan. 18, 1991, abandoned.

[51] Int. Cl.$^6$ .................................................. A61B 5/0428
[52] U.S. Cl. .................................................. 128/696
[58] Field of Search .................................................. 128/696

[56] References Cited

U.S. PATENT DOCUMENTS

| | | |
|---|---|---|
| 3,848,586 | 11/1974 | Suzuki et al. . |
| 3,889,108 | 6/1975 | Cantrell . |
| 3,972,000 | 7/1976 | Desblache et al. . |
| 4,352,182 | 9/1982 | Billi et al. . |
| 4,417,102 | 11/1983 | Allen . |
| 4,458,691 | 7/1984 | Netravali . |
| 4,458,692 | 7/1984 | Simson . |
| 4,492,235 | 1/1985 | Strick . |
| 4,633,884 | 1/1987 | Imai et al. . |
| 4,649,505 | 3/1987 | Zinser, Jr. et al. . |
| 4,660,163 | 4/1987 | Fukasawa et al. . |
| 4,684,922 | 8/1987 | Minogue . |
| 4,696,059 | 9/1987 | MacDonald et al. . |
| 4,707,786 | 11/1987 | Dehmer . |
| 4,779,617 | 10/1988 | Whigham . |
| 4,791,672 | 12/1988 | Numely . |
| 4,802,222 | 1/1989 | Weaver . |
| 4,841,828 | 6/1989 | Suzuki . |
| 4,853,969 | 8/1989 | Weldman . |
| 4,893,632 | 1/1990 | Armington . |
| 4,912,758 | 3/1990 | Arbel . |
| 4,947,432 | 8/1990 | T pholm . |
| 4,947,435 | 8/1990 | Taylor . |
| 4,947,858 | 8/1990 | Smith . |

*Primary Examiner*—William E. Kamm

[57] ABSTRACT

An apparatus and method directed to an adaptive noise filtering arrangement. The arrangement has the ability to estimate a first set of data for a first time-dependent variable based upon at least two sets of data for two time-dependent variables related to the first time-dependent variable. Additionally, the arrangement has the ability to filter an actual set of data for the first time-dependent variable based upon the first set of data and the actual set of data. The estimated first set of data and filtered actual set of data can be printed or displayed in a graphical format for analysis.

39 Claims, 6 Drawing Sheets

FILTER APPARATUS AND METHOD FOR REDUCING SIGNAL NOISE USING A PLURALITY OF SIGNALS OBTAINED FROM A SIGNAL SOURCE

CROSS REFERENCE TO RELATED APPLICATION

The present application is a continuation application of U.S. patent application Ser. No. 08/071,337, filed Jun. 2, 1993, now U.S. Pat. No. 5,421,342 issued Jun. 6, 1995, which application is a continuation application of U.S. patent application Ser. No. 07/643,719, filed Jan. 18, 1991, now abandoned.

TECHNICAL FIELD

This invention relates to an apparatus and method for increasing the signal-to-noise ratio of a signal, and, more particularly, to an adaptive noise filtering arrangement utilizing at least two sets of data representative of a single time-dependent variable to produce a filtered signal representative of the variable.

BACKGROUND OF THE INVENTION

In general, noise filtering is important in a number of signal processing areas including electrocardiology, electroencephalography, sound amplification, data transmission and communications. By providing the appropriate noise filtering, a particular signal can be utilized in a manner such that the undesirable effects of noise are substantially eliminated.

By way of example, recorded components of an electrocardiographic (ECG) signal (P-waves, for example) are frequently difficult to observe unambiguously due to effects such as noise, superposition on other ECG signals (T-waves, for example), or unusually low amplitudes. Improving the signal-to-noise ratio of an ECG signal allows the characteristics of a P-wave, which is typically masked by noise, to be better detected and identified. Also, electrocardiographic micropotentials, which usually require signal averaging to detect, may be further enhanced by using the appropriate filtering to compare multiple averages.

Another problem encountered when recording the components of an ECG signal is the effect of noise on QRS detection. More specifically, arrhythmia monitoring is plagued by false-positive QRS detection caused by noise artifacts of non-cardiac origin. For example, the source of such noise artifacts may be from skeletal muscle action. In addition, arrhythmia monitoring is dependent upon the ability to accurately determine the characteristics of P-waves. Accurate detection of P-waves is central to correct arrhythmia classification.

Thus, while various arrangements are available for filtering ECG signals, there remains a need for improving the signal-to-noise ratio of ECG signals to permit the accurate determination of the characteristics of ECG signals such as P-waves. There also remains the need for filtering which can also be used for wave delimiting or wave onset/offset detection, reducing noise while maintaining diagnostic bandwidth, and improving data compression efficiency for transmission and/or signal storage. In addition, there remains the need for filtering which provides differentiation of signal origin to parts of the heart, electrode misplacement detection, discrimination of true ECG change from electrode position effects, recreation of missing leads, event detection of power parameters, and non-cardiac signal detection, such as fetal ECG.

SUMMARY OF THE INVENTION

According to the invention a system for increasing the signal-to-noise ratio of a signal such as a reference signal representative of a time-dependent variable, the system has a first lead arranged to monitor the variable and generate a reference signal and a second lead arranged to monitor the variable and generate an alternate signal. The system also has a sampler which samples the reference signal to generate a reference set of values associated with a selected reference value of the set. The system also samples the alternate signal to generate an alternate set of values associated with the selected reference value. Finally, the system has means for calculating a compliance coefficient based upon the reference set and the alternate set and means for calculating a filtered value of the reference signal based upon the selected reference value and the compliance value.

Further, according to the invention, a system for increasing the signal-to-noise ratio of a reference signal representative of a waveform emanating from a heart has a first ECG electrode located at a first location relative to the heart to monitor the waveform and to generate the reference signal. The system also has a plurality of alternate ECG electrodes, each alternate ECG electrode being located at a unique ECG electrode location relative to the heart to monitor the waveform and generate an alternate signal, as well as a sampler which samples each alternate signal to generate respective sets of alternate values. In addition, the system has means for generating an estimated set of values associated with the first ECG electrode location based upon the respective sets of alternate values, wherein the estimated set of values represents the waveform, means for sampling the reference signal to generate a reference set of values associated with a selected reference value of the set, means for calculating a compliance coefficient based upon the reference set and the estimated set, and means for calculating a filtered value of the reference signal based upon the selected reference value and the compliance value.

Another aspect of the system for increasing the signal-to-noise ratio of a reference signal representative of a time-dependent variable has a lead disposed to monitor the time-dependent variable and generate a reference signal and a sampler which samples the reference signal during a first period of time to generate a reference set of values associated with a selected reference value of the set. The system also has means for sampling the reference signal during a second period of time to generate an alternate set of values associated with the selected reference value, means for calculating a compliance coefficient based upon the reference set and the alternate set, and means for calculating a filtered value of the reference signal based upon the selected reference value and the compliance value.

In another aspect of the invention a system is provided for generating an estimated set of values representative of a time-dependent variable emanating from a source, wherein the values of the time dependent variable are associated with a lead location relative to the source. A plurality of leads are disposed to monitor the time-dependent variable, each lead being located at a unique lead location relative to the source and each lead generating a reference signal. The system also comprises means for sampling each reference signal to generate respective sets of reference values, and means for generating an estimated set of values associated with the lead location based upon the respective sets of reference values, wherein the estimated set of values is representative of the variable.

In another aspect, a system for increasing the signal-to-noise ratio of a reference signal representative of a time-dependent variable emanating from a source, has a first lead positioned at a first location relative to the source to monitor the time-dependent variable and generate the reference signal. The system also has a plurality of alternate leads, wherein each alternate lead is positioned at a lead location relative to the source to monitor the time-dependent variable and generate an alternate signal. In addition, the system has means for sampling each alternate signal to generate respective sets of alternate values and means for generating an estimated set of values associated with the first lead location based upon the respective sets of alternate values, wherein the estimated set of values is representative of the time-dependent variable. Finally, the system has means for sampling the reference signal to generate a reference set of values associated with a selected reference value of the set, means for calculating a compliance coefficient based upon the reference set and the estimated set and means for calculating a filtered value of the reference signal based upon the selected reference value and the compliance value.

In another aspect of the invention, a system for increasing the signal-to-noise ratio of a reference signal representative of a waveform produced by a heart has a first ECG electrode disposed to monitor the waveform and generate the reference signal, a second ECG electrode disposed to monitor the waveform and generate an alternate signal and means for sampling the reference signal to generate a reference set of values associated with a selected reference value of the set. The system also has a sampler for sampling the alternate signal to generate an alternate set of values associated with the selected reference value, means for calculating a compliance coefficient based upon the reference set and the alternate set, and means for calculating a filtered value of the reference signal based upon the selected reference value and the compliance value.

In another aspect of the invention, a system is provided for generating an estimated set of values representative of a waveform emanating from a heart. The values are associated with an ECG electrode location relative to the heart. The system has a plurality of ECG electrodes, each electrode being located at a unique ECG electrode location relative to the heart to monitor the waveform and generate a reference signal. The system also has sampling means for sampling each reference signal to generate respective sets of reference values, and means for generating an estimated set of values associated with the ECG electrode location based upon the respective sets of reference values, wherein the estimated set of values is representative of the waveform.

Finally the invention provides a method for increasing the signal-to-noise ratio of a reference signal generated by a first lead for monitoring a time-dependent variable. The method includes the steps of sampling the reference signal during a first period of time to generate a reference set of values associated with a selected reference value of the set and sampling the reference signal during a second period of time to generate an alternate set of values associated with the selected reference value. The method also comprises calculating a compliance coefficient based upon the reference set and the alternate set and calculating a filtered value of the reference signal based upon the selected reference value and the compliance value.

BRIEF DESCRIPTION OF THE DRAWINGS

Preferred exemplary embodiments of the invention will be described in conjunction with the appended drawings, wherein like numerals denote like elements, and:

FIG. 1A illustrates a system for monitoring ECG signals from a person;

DETAILED DESCRIPTION OF THE PREFERRED EXEMPLARY EMBODIMENT

Figure 1B:
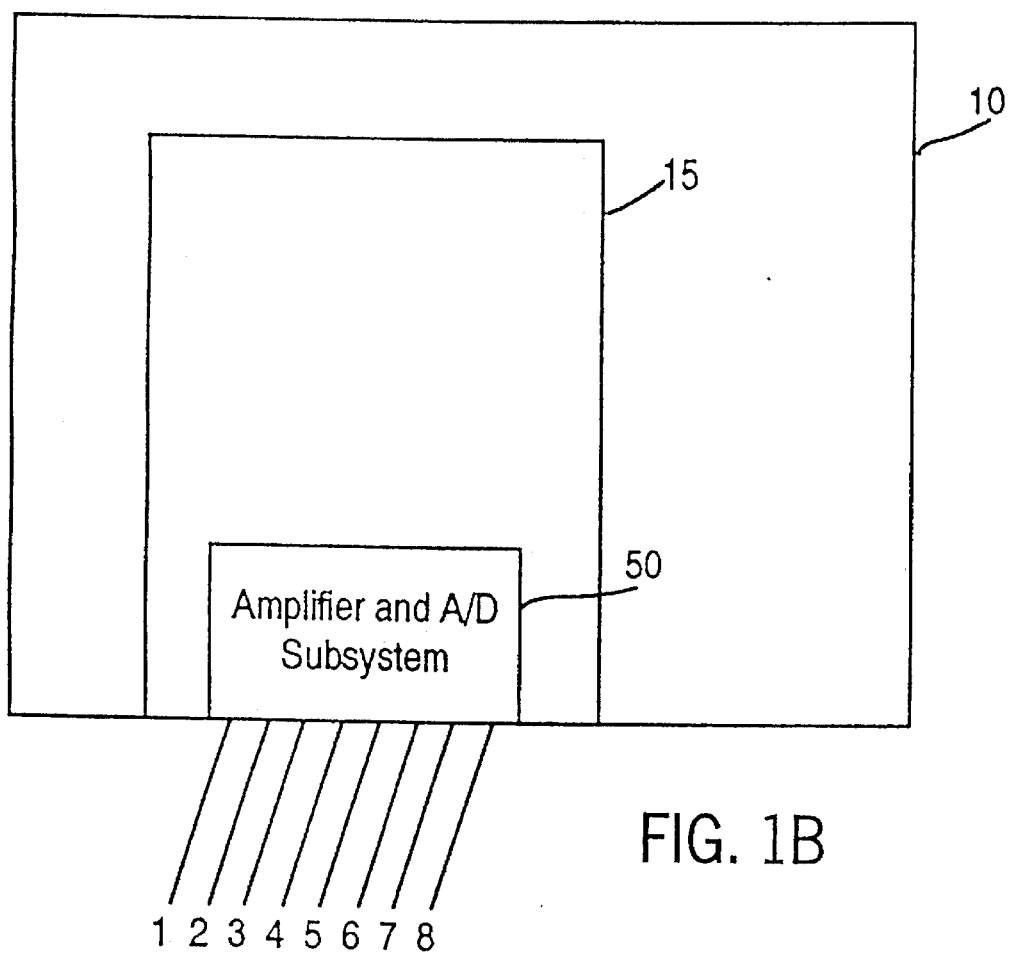
FIG. 1B is a block diagram representative of a processing portion of the system.

FIG. 1A generally illustrates a system for monitoring the ECG signals from a person. This system includes a microcomputer 10 coupled to eight ECG electrodes via an interface board acting as an amplifier and A/D subsystem 50 (FIG. 1B). By way of example only, the system may be an X-Scribe system produced by Mortara Instrument, Inc. In the X-Scribe system, the microcomputer may take the form of an IBM PS/2 Model 30, and the interface board may take the form of a PC-ECG™ data acquisition board manufactured by and available from Mortara Instrument, Inc. The PC-ECG™ interface board includes an eight bit connector which is compatible with either an eight bit or sixteen bit expansion slot of the expansion bus in a typical personal computer such as the PS/2 Model 30. The PC-ECG™ interface board can be coupled to twelve ECG electrodes and provide the data from these electrodes to the microcomputer via the expansion bus. Additionally, the PC-ECG™ interface board comprises a microprocessor (Motorola 68000), ROM, RAM, an analog-to-digital converter and associated circuitry. The microprocessor of the PC-ECG™ board can be programmed by downloading appropriately formatted code from microcomputer 10 to the board RAM using the Load software provided with, for example, the X-Scribe system.

In the preferred embodiment of the system, code for an ECG lead estimation operation and ECG filtering operation is down loaded onto the PC-ECG™ interface board via microcomputer 10. The source code for this code is listed in the attached as Appendix A and includes lines 1–641. The source code is written in the C-language and is discussed in detail below. First, however, the general concepts behind the filtering operation will be discussed.

Figure 2:
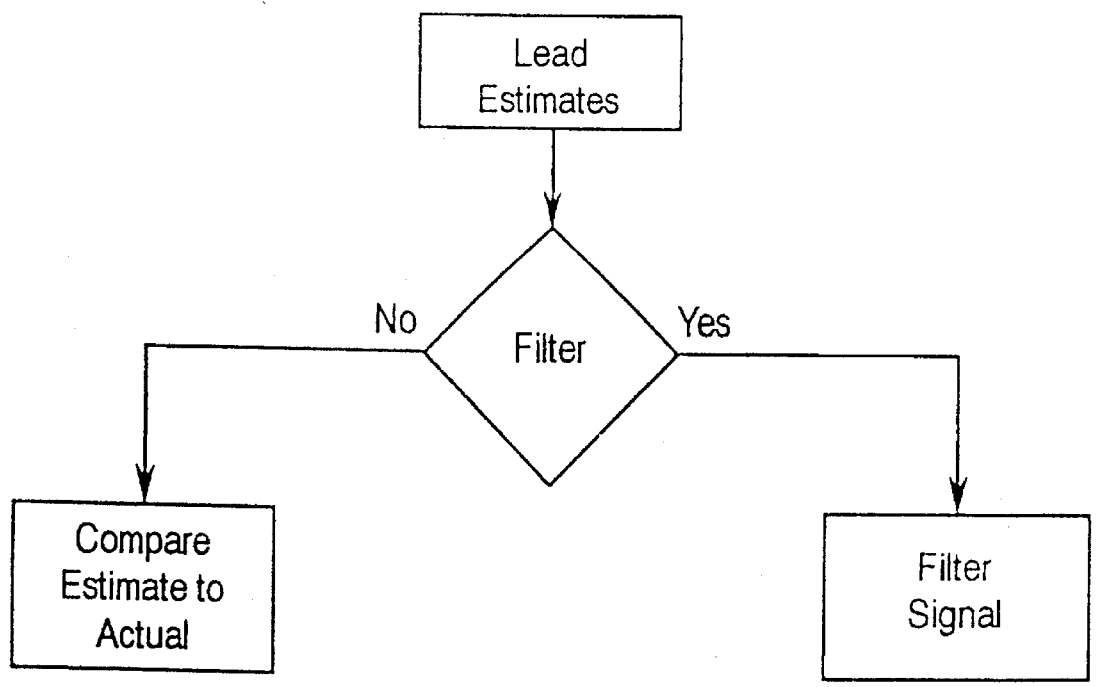
FIG. 2 illustrates the estimation process as used for both predicting missing or damaged leads as well as for filtering an actual time-dependent signal.

The ECG lead estimation operation can be used either for filtering or predicting operation of particular leads, as discussed below and shown in FIG. 2. ECG lead estimation allows the system user to estimate an alternate set of time-dependent values for one ECG lead based upon the values monitored by the other ECG leads. More specifically, in an eight lead system, the system user would have the ability to estimate the time-dependent values of signals from any one of the eight leads based upon the actual time-dependent values for the other seven leads. One use of this feature is to provide the user an estimate for the time-dependent values of an ECG lead in the situation where the user has the need to compare the actual time based values for the particular ECG lead. For example, during the course of monitoring ECG leads coupled to a person, the system may question whether or not the time based values provided by a particular ECG lead are reasonable. Another use for this operation is to provide an alternate time-dependent set of values for a particular ECG lead for purposes of filtering the actual time-dependent values for that particular ECG lead.

For predicting operation of a particular lead, alternate time-dependent values from a number of arrays equal to the total number of leads, NLD minus one (NLD−1) are used, where NLD is the total number of leads (including the defective or missing lead or lead whose values are to be filtered). The arrays may be NSMPL dimensional arrays, where NSMPL is the number of actual time-dependent values sampled during a particular time frame. From these arrays, a coefficient matrix (discussed in detail below) is determined. Calculating the coefficient matrix corresponds to calculating a series of estimated alternate time dependent values, which can in turn be compared to the actual time-dependent values output by the defective or missing lead.

Therefore, the filtering operation uses estimated alternate time-dependent values generated by the estimation operation for a particular ECG lead along with actual time-dependent values for that particular ECG lead in order to provide a set of filtered time-dependent values which substantially remove noise artifacts of non-cardiac origin. The noise filtering uses the coefficient matrix to perform the filtering operation as follows.

Once the coefficient matrix is obtained, the leads are sampled and calculated at each moment in time corresponding to the index i=1,2 ... The coefficient matrix is then used along with data subsequently sampled at time, $1=1,2,\ldots$ to yield a compliance factor from which a filtered output point is determined.

As discussed above, intrinsic to the filtering operation is the calculation of compliance factors used to calculate the filtered signal on a point by point basis. Hence, once the coefficient matrix has been determined, the filtered signal can be calculated in real time. If the locations of the leads are changed, a new coefficient matrix must be determined. Then a composite of the values of the signals output from the leads in the new location can be used to develop the estimated alternate time-dependent values. Table 1 provides a list of mathematical representations which will be used to describe how the compliance factors are calculated using the estimated signal process.

TABLE 1

| i: | Sample sequence index (integer) |
|---|---|
| l,m,n: | Input leader sensor indices (integer) |
| l' | The particular lead to be filtered |
| NSMPL: | Number of sample points taken by each lead to determine the coefficient matrix C(l,m) (i = 1 ... NSMPL) |
| NLD: | Number of leads or sensors (l,m,n = 1 ... NLD) |
| z(i,l): | Actual time-dependent valves (Sample data points for simultaneous inputs) |
| dz(i,l): | z(i,l) − z(i − 1,l) Sample-to-sample difference |
| c(l,m): | Coefficient matrix. The diagonal elements C(l,l) are fixed at −1. |
| u(i,l): | Estimated alternate time-dependent values |

TABLE 1-continued

| i: | Sample sequence index (integer) |
|---|---|
| du(i,l): | u(i,l) − u(i − 1,l) estimate-to-estimate difference |

The object of the estimated signal process is to find the "best" solution for a set of coefficients called the coefficient matrix C(l,m) such that the differences between the estimated alternate time-dependent values and the actual time-dependent values are minimized as defined below. Equation (1) expresses this algebraically.

The "best" solution is taken to be the coefficient matrix C(l,m) which minimizes the left-hand side of Equation (1), $$dev(i,l) = u(i,l) - z(i,l) = \sum_{m=1}^{NDL} C(l,m)z(i,m) \quad (1)$$

wherein minimization refers to minimizing the mean square of the left-hand side of Equation (1), i.e., dev(i,R) for each sample i=i, ... ,NSMPL. Hence, the average or difference between the estimated alternate time-dependent values u(i,l) and the actual time-dependent values z(i,l) is minimized.

Different leads corresponding to different values of 1 are subject to arbitrary offsets in their corresponding actual time-dependent values z(i,l). Therefore, it is advantageous to use the estimate-to-estimate difference du(i,l) and the sample-to-sample difference dz(i,l) and minimize each squared error, Esum(l) for i=i ... NDL, as shown Equation (2), in order to obtain the coefficient matrix C(l,m).

$$Esum(l) = \sum_{i}^{NSMPL} (dev(i,l))^2 \quad (2)$$

Hence, the lth row of coefficient matrix C (l,m) is that set of coefficients which minimizes the value of Esum(l).

In certain situations the actual time-dependent values z(i,l) may not be independent for various leads (values of 1). This can occur if, for example, lead 1 (l=1) and lead 2 (l=2) are sampled by an analog-to-digital converter (ADC) with inputs that are not completely electrically isolated. When the actual time-dependent values are not independent, there may not be a unique solution for the coefficient matrix C(l,m), a situation referred to as "degeneracy". This ambiguity is resolved by choosing the coefficient matrix C(l,m) which has the smallest sum of squares of each of the elements of the coefficient matrix C(l,m). This can be achieved by minimizing a new error function, Fsum(l) for l=1,. . . NDL defined in Equation (3).

$$Fsum(l) = Esum(l) + wt \sum_{m=1}^{NDL} [C(l,m)]^2 \quad (3)$$

Here, wt is a weight factor determined by later considerations. The purpose of the wt is to maintain a fixed relationship between the relative weight given to the terms in Fsum(l). Minimization of Fsum(l) with respect to C(l,n) is accomplished by setting the partial derivatives of Fsum(l) with respect to C(l,n) to zero. The diagonal elements, C(l,l), are not considered variable, and are fixed at a value of −1. The partial derivative of Fsum(l) with respect to C(l,n), set to zero, results in Equation (4).

An expression for C(l,n) can be obtained from Equation (3) as shown in Equation 4.

$$C(l,n) = \sum_{m=1}^{NDL} M^{-1}(n,m)V(m)$$

-continued $$\text{where } M(m,n) = wt \cdot d(m,n) + \sum_{i=1}^{NSMPL} dz(i,m)dz(i,n),$$

$$\text{and } V(m) = \sum_{i=1}^{NSMPL} dz(i,l)dz(i,m),$$

$$\text{and } d(m,n) = \begin{cases} 1 \text{ if } m = n \\ 0 \text{ if } m \neq n, \end{cases} \quad (4)$$

and m and n take on all values from 1 to NLD except l', where l' is the lead to be estimated,
and $M^{-1}(n,m)$ is the inverse of matrix $M(m,n)$,
and M is a NLD-1×NLD-1 dimensional matrix.

It is economically desirable to accomplish these calculations, including the inversion of matrix $M(m,n)$ in fixed point arithmetic. To facilitate this, the trace of the matrix $M(m,n)$ (without the wt term added to the diagonal of $M(m,n)$) is determined. Then, a shift normalization necessary to insure that the trace of $M(m,n)$ lies between 8192 and 16384 can be established. Namely, the matrix $M(m,n)$ and the vector $V(m)$ are scaled by shifting (dividing by the appropriate power of 2). After the normalization is complete, $M(m,n)$ and $V(m)$ are nearly "dimensionless", in the sense that their magnitude is nearly independent of the values of the actual time-dependent values $z(i,l)$.

The weight wt is then chosen to be 1/128 of the trace of $M(m,n)$. This maintains a fixed relationship between the relative weight given to the terms in Fsum above. The process of inverting the matrix $M(m,n)$ returns a solution for the $l^{th}$ row of the coefficient matrix $C(l,m)$. This process is repeated for l=1 . . . NLD yielding all NLD rows of the coefficient matrix $C(l,m)$. Finally, the resulting coefficient matrix $C(l,m)$ is scaled up by 256 to improve subsequent arithmetic accuracy.

The filtering operation for the first embodiment of the invention involves independently filtering two separate frequency bands f1 and f2. Table 2 shows several intermediate terms y, y2, y3, y', y'2, y'3' which must first be calculated.

TABLE 2

| | |
|---|---|
| y'(i,l) = | $\sum_{m=1}^{NLD} C(l,m)z(i,m)$ |
| y(i,l) = | y'(i,l) + 2z(i,l) |
| y2'(i,l) = | (y'(i,l) + y'(i − 1,1))/2 |
| y2(i,l) = | (y(i,l) + y(i− 1,1))/2 |
| y8'(i,l) = | (y2'(i,l) + y2'(i − 2,l) + y2'(i − 4,l) + y2'(i − 8,l))/8 |
| y8(i,l) = | (y2'(i,l) + y2(i − 2,l) + y2(i − 4,l) + y2(i − 8,l))/8 |

The high pass filters f1 and f2 are then defined by Equations (5a) and (5b), respectively.

$$\begin{aligned}
f1(i-4,l) &= y(i-4,l) - 3/4 \times (y2(i-2,l) + \\
&\quad y2(i-5),l)) + 1/4 \times (y2(i,l) + \\
&\quad y2(i-7,l))
\end{aligned} \quad (5a)$$

$$\begin{aligned}
f2(i-16,l) &= y(i-16,l) - 11/16 \times (y8(i-8,l) + \\
&\quad y8(i-17,l)) + 3/16 \times (y8(i,l) + \\
&\quad y8(i-25,l)) - f1(i-16,l)
\end{aligned} \quad (5b)$$

In addition, high pass filters f1'(i-4,l) and f2'(i-16,l) are defined analogously to f1(i-4,l) and f2(i-16,l) with y'(i,l), y2'(i,l) and y8'(i,l) substituted for y(f,l), y2(i,l) and y8(i,l), respectively. It should be noted that y and y' correspond to the sum and difference, respectively, of the estimated alternate time-dependent values u(i,l) and the actual time-dependent values z(i,l). A similar relationship exists between the f1 and f1', and between the f2 and f2' teams.

Computationally, the evaluation of y'(i,l) in Table 2 involves the largest number of calculations, namely it involves NLD multiplications for each of the NLD leads or sensors. However, this computation need only be carried out one time for each sample interval NSMPL and need not be repeated for each pass f1, f2. As a result, this multi-band filtering technique is computationally economic once the estimated alternate time-dependent values u(i,l) have been calculated for a given lead or sensor l.

Figure 3A:
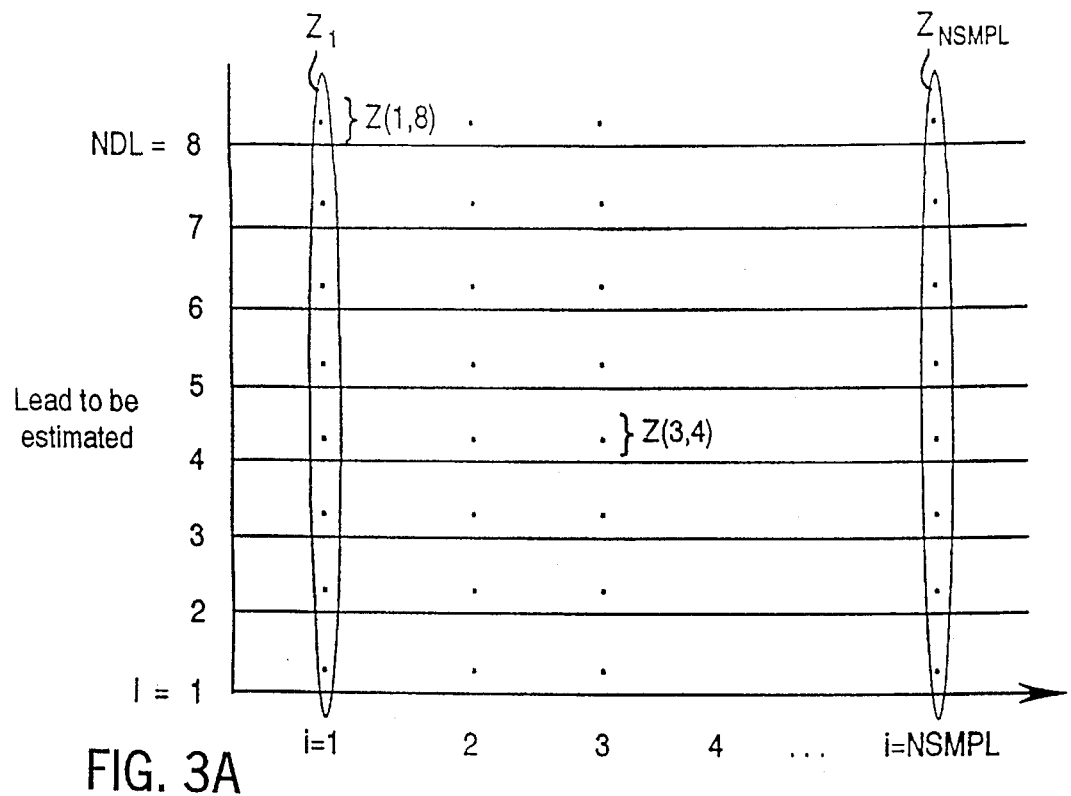
FIG. 3 illustrates a representation of the computation of the vectors Zi and Ui.
Figure 3B:
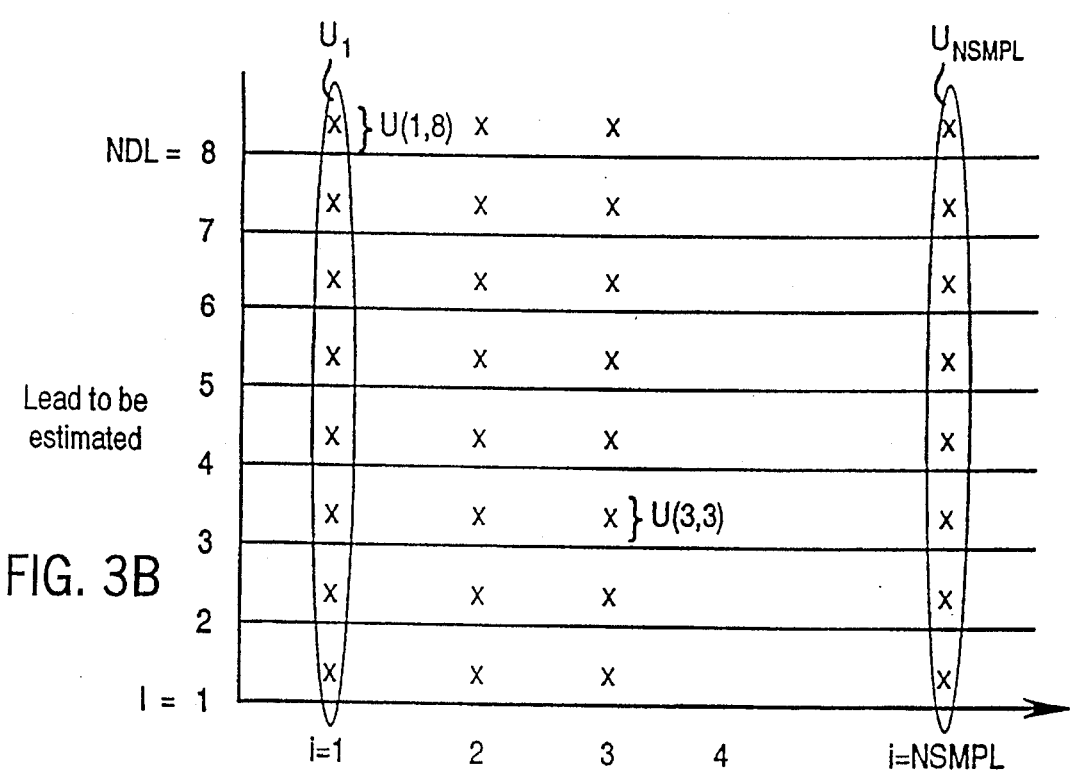

Two different versions of compliance factors yielding substantially the same result are written here as $\rho_1(i)$ and $\rho_2(i)$, where i is an integer corresponding to the sample sequence index as indicated in Table 1. Equations (6a) and (6b) show how the compliance factors $\rho_1(i)$ and $\rho_2(i)$ are calculated using the actual time-dependent values $z(i,l)$ and the estimated alternate time-dependent values $u(i,l)$. The version $\rho_2(i)$ is used in the preferred embodiment. Equations (6a) and (6b) can be written in vector form using scalar products as shown in Equations (7a) and (7b), respectively, where $U_i$ and $Z_i$ correspond to vectors of dimension NLD formed by taking the $i^{th}$ estimated alternate time-dependent values u(i,l) and the $i^{th}$ actual time-dependent values z (i,l), respectively for all leads l=1 . . . NLD as shown in FIG. 3.

Computation of the scalar products $U_i \cdot Z_i$, $Z_i \cdot Z_i$ and $U_i \cdot U_i$ involves only one new product for each new sample.

$$\rho_1(i) = \frac{\sum_{l=1}^{NDL} u(i,l)z(i,l)}{\sum_{l=1}^{NDL} z^2(i,l)} \quad (6a)$$

$$\rho_2(i) = \frac{\sum_{l=1}^{NDL} u(i,l)z(i,l)}{\sum_{l=1}^{NDL} (u^2(i,l) + z^2(i,l))} \quad (6b)$$

$$\rho_1(i) = \frac{U_i \cdot Z_i}{Z_i \cdot Z_i} \quad (7a)$$

$$\rho_2(i) = \frac{2U_i \cdot Z_i}{U_i U_i + Z_i Z_i} \quad (7b)$$

FIG. 3 shows the relationship between the actual time-dependent values z(i,l) and the NLD dimensional vectors $Z_i$, and the relationship between the estimated alternate time-dependent values u(i,l) and the NLD-1 dimensional vectors $U_i$, where NLD=8. The top of FIG. 3 shows selection of the vectors Zi and the bottom of FIG. 3 shows selection of the vectors Ui. The lead to be estimated is lead 5 (l=5) in FIG. 3.

The filtered signal outputs $g_{j,k}(i,l')$ and $g'_{j,k}(i,l)$ are calculated as shown in Equation (8).

$$g_{j,k}(i,l')=\rho_j(i)f_k(i,l') \quad (8)$$

$$g'_{j,k}(i,l')=\rho_j(i)f'_k(i,l')$$

where j=1 or 2; k=1 or 2; i=1 . . . ; l=1 . . . NLD. Here f1, f2, f$_1$ and f$_2$ are calculated as described above using Table 2 and Equations (5a) and (5b).

The values of $g_{j,k}$ and $g'_{j,k}$ are displayed upon the monitor of microcomputer 10. Referring to lines 627–638 of the code, an interrupt is sent to microcomputer 10 from the PC-ECGTM board for each sample i subsequent to the calculation of $g_{j,k}$ and $g'_{j,k}$. At the interrupt, microcomputer 10 updates its video memory such that the display displays an graphic real-time representation of the filtered signal corresponding at lead l'. More specifically, every 4 milliseconds an interrupt is sent to microcomputer 10. For convenient graphics control, microcomputer 10 buffers 16 filtered output signals ($g_{j,k}$, $g'_{j,k}$) prior to updating its video memory, thereby updating the video memory and image displayed upon the monitor every 64 milliseconds.

Of course, other approaches could be taken for purposes of displaying the filtered output signals. For example, the microcomputer 10 could be configured to provide graphical data representative of the filtered output signals to a printer connected to microcomputer 10.

The calculation of the coefficient matrix C(l,m), the compliance factors $f_1(i)$, $f_2(i)$ and the filters $f_1$, $f_2$, $f'_1$ and $f'_2$ will now be described in accordance with the source code in Appendix A and the preferred embodiment.

Table 3 matches up nomenclature used in the source code and the corresponding nomenclature used in the above-discussed equations. In the preferred embodiment there are eight leads or sensors so NLD is 8. The number of samples NSMPL is 1,000. The procedure "pcmain" begins at line 79 of the source code and ends at line 256 of the code.

The interrupt function "ampirq" in the code enables the PC-ECG™ interface board to accept interrupts from the amplifier and A/D subsystem 50 at 1 millisecond intervals. The amplifier and A/D system interrupts with 18 byte data frames in FIFO using "amp.fifo.byte" (see Table 3). Each frame consists of a "synch" byte plus 16 data bytes (8 leads X 2 bytes) as well as a status byte (not used here). The synch byte plus the 8 bytes of data from the 8 leads are read into address "pzbi" by a pre-interrupt function.

The pointer "pzbi" is used as a circular buffer pointer. The data from the 8 leads enter the FIFO memory every millisecond. The data are then averaged every four milliseconds to net one sample or actual time-dependent value z(i,l) every four milliseconds for every lead.

Finally, the function "ampirq" calls the function "irq250" which begins at line 357 and ending at line 640 in the source code. The function "irq250" performs the calculations corresponding to equations (5)–(13) as well as the calculations in Table 2. At line 392 of "irq250" performs the test of whether or not the coefficient matrix has been calculated in "pcmain". Once "ready" is set to 1 at line 261 in "pcmain", "irq250" goes on to calculate $f_1$, $f_2$, $\rho_1$, $\rho_2$ and finally $g_{j,k}$, $g'_{j,k}$.

Figure 4:
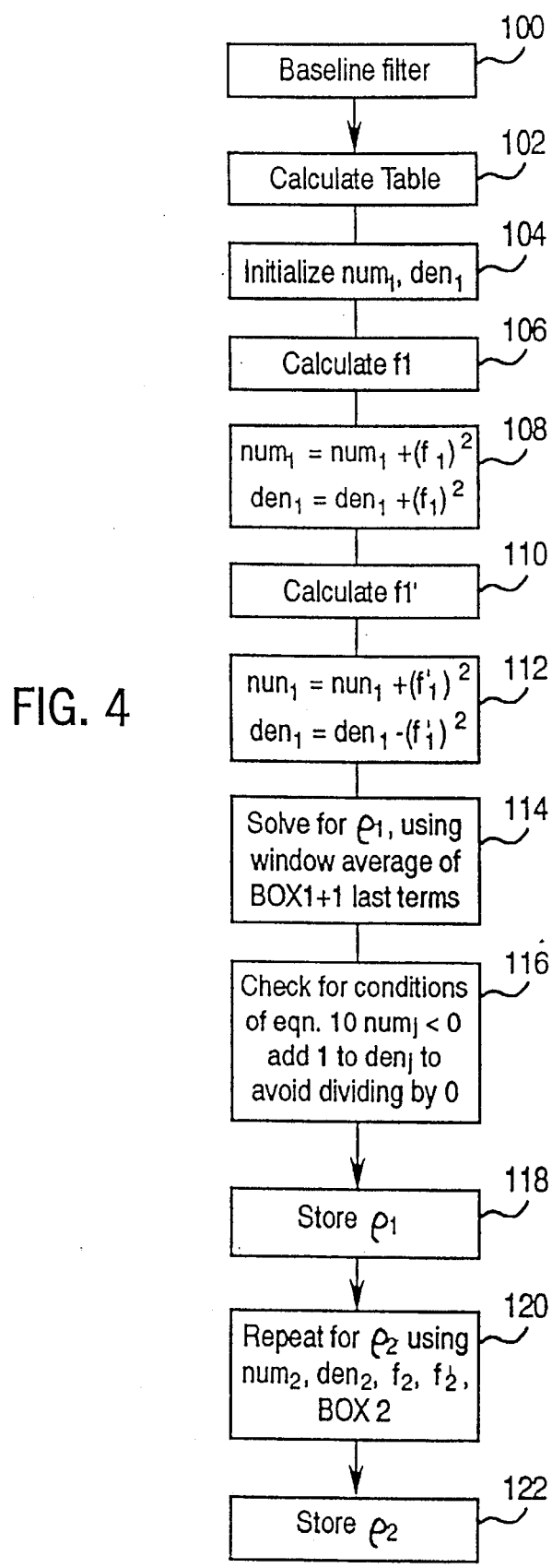
FIG. 4 is a flow chart illustrating the calculation of the compliance factors $\rho_1(i)$ and $\rho_2(i)$.

FIG. 4 is a flow chart outlining the steps "irq250" uses to calculate the compliance factors $\rho_1$ and $\rho_2$. More specifically, step 100 performs a baseline high pass filter on the raw data. Step 102 calculates the expressions in Table 2. Step 104 initializes $num_1$ and $den_1$. Step 106 involves calculating f1 according to Equation (5a). Step 108 and 110 involve calculating f1'. Steps 112–116 involve calculating $\rho_1(i)$ by substituting the result of Equation (9) into Equation (10). The value of $\rho_1(i)$ is then stored in step 118, and the process is repeated in step 120. In step 120, $num_2$, $den_2$, f2, f2' and BOX2 are substituted in place of $num_1$, $den_1$, f1, f1', and BOX1 respectively, and steps 104–116 are executed to solve for $\rho_2(i)$. Finally, in step 122 the values of $\rho_2(i)$ are stored.

TABLE 3

| Specification or Explanation | Appendix A |
| --- | --- |
| $\rho_1$, $\rho_2$ | rho[0], rho[1] |
| C(l,m) | coef[u] u = 0 . . . 63 |
| V(m) | ivect[u] u = 0 . . . 6 |
| M(m,n), $M^{-1}$(n,m) | corr[u], icorr[u] |
|  | u = 0 . . . 47 |
| $num_1$, $num_2$ | numer[0], numer[1] |
| $den_1$, $den_2$ | denom[0], denom[1] |
| NSMPL | NSMPL |
| NLD | NLD |
| Box1 Box2 | Box1 = 8 Box2 = 32 |
| y, y', y, y2', y8, y8' | x, xp, x2, xp2, x8, xp8 |

TABLE 3-continued

| Specification or Explanation | Appendix A |
| --- | --- |
| F1 F2 | f1 f2 |
| $\sum_{k=i-(Box1+1)}^{k=i-1} num_1(k)$, | numer[0], denom[0] |
| $\sum_{k=i-(Box1+1)}^{k=i-1} den_1(k)$ |  |
| $\sum_{k=i-(Box2+1)}^{k=i+1} num_2(k)$ | numer[1], denom[1] |
| $\sum_{k=i-(Box+1)}^{k=i+1} den_2(k)$ |  |
| interrupt to pc indicating filtered output is ready | amp.pcin.byte |
| circular filtered output | xout |
| filter signals | f1out, f2out |
| circular buffer pointer | pzbi |
| raw input data for each lead | zin[u], u = o . . . 8 |

The matrix M in equation (5) is a 7×7 matrix and the vector V is a 7 dimensional vector. The matrix M corresponds to the array "corr" of dimension 49 defined at line 60 of the code. The vector V corresponds to the array "ivect" defined at line 61 of the code. In calculating the coefficient matrix C(l,m) a set of data z(i,l) i=1 . . . 1,000 and l=1 . . . 8 is first sampled and sample-to-sample difference terms dz(i,l) are stored in the RAM of the A/D subsystem 50 of the PC-ECG™ interface board. The RAM is a circular buffer memory. Since NLD=8, the coefficient matrix C(l,m) is an 8×8 matrix, which is represented in the code by a 64 element array called "coef" defined at line 60.

Figure 5:
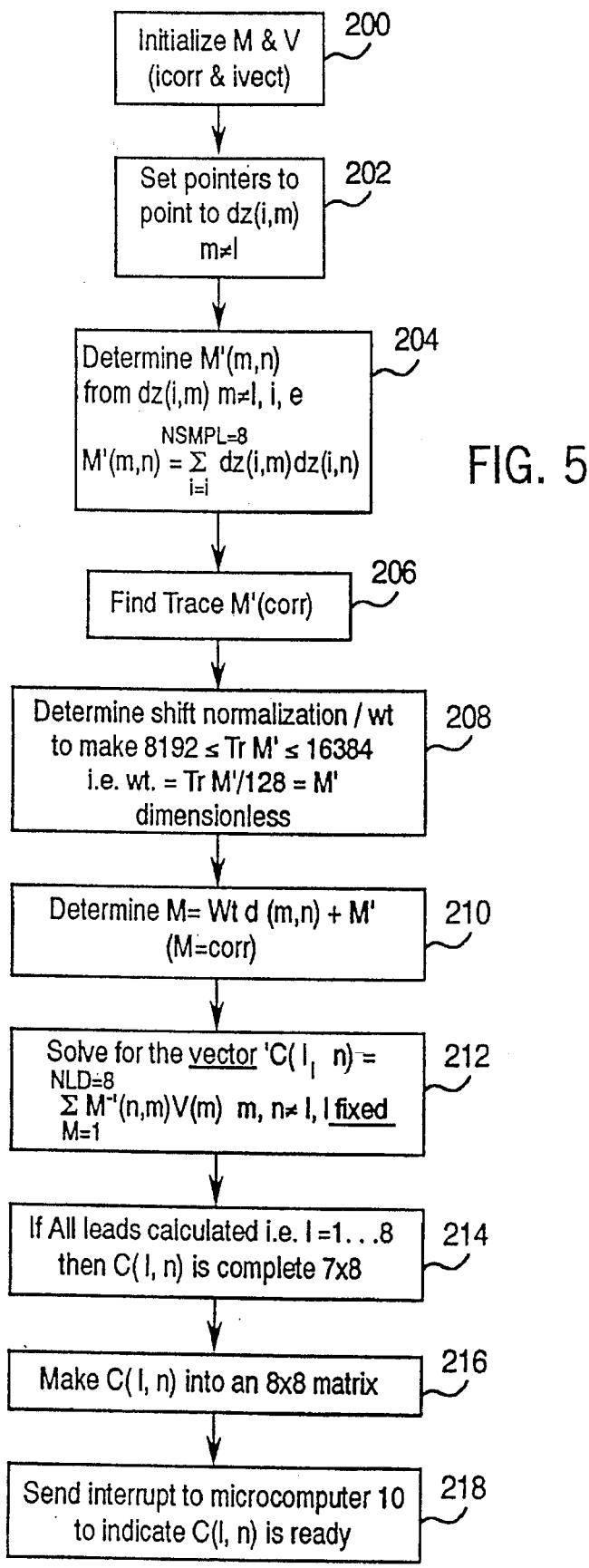
FIG. 5 is a flow chart illustrating the calculation of the coefficient matrix $C(l,n)$.

FIG. 5 shows a flow chart directed to calculating the coefficient matrix C(l,m). (The line numbers corresponding to the source code which implements the steps discussed below are included parenthetically at the introduction of each step.)

The process begins by initializing "corr" (M) and "ivect" (V) at step 200 (lines 151–153). Step 202 involves setting pointers to point to the sample-to-sample differences dz(i, m). Step 204 (lines 160–187) involves calculating the product of sample-to-sample differences dz(i,m) contained in the second term on the right-hand side of the expression for M(m,n) in Equation (4). This results in a matrix M'(m,n) which is again stored as "corr". Step 206 (line 104) involves finding the trace of matrix M'(m,n). Step 208 (lines 202–203) involves determining the shift normalization or wt in the first term of the right-hand side of Equation M(m,n) in Equation (4). Therefore, after step 208 is complete, the matrix M'(m,n) is dimensionless, i.e., independent of the scale of the actual time-dependent values z(i,l). Step 210 (lines 220–228) involves calculating the matrix M(m,n) in Equation (4). Finally, step 212 (line 239) inverts the matrix M(m,n) in order to calculate C(l,n). Here C(l,n) is for a fixed l or a single lead or sensor, and therefore C(l,n) is a vector of dimension NLD−1=7.

Steps 200–212 must be repeated for all of the leads l=1. . . NLD=8 yielding a 7×8 matrix C(l,n) at step 214 (lines 254–265). In step 216 the 7×8 matrix becomes the completed 8×8 matrix C(l,n) by inserting −1 in the diagonal of the 7×8 matrix. The 8×8 coefficient matrix C(l)m) can then be used to calculate y'(i,l) in Table 2. Upon completion of 8×8 matrix C(l,n) an interrupt to microcomputer 10 in step 218 takes place.

In order to calculate y'(i,l) another set of actual time-dependent values z(i,m) must be sampled by the analog-todigital (A/D) subsystem. Once y'(i,l) along with y, y2', y2, y8' and y8 are all calculated according to the expressions in Table 2, the filters f1, f2, f2', and f2' can be determined. Note that the matrix multiplication used to obtain y' need only be done one time for all of the filters as was previously discussed. Consequently, multi-bin filtering is computationally economic once the estimated signal input corresponding to the matrix C(l,m) is calculated.

The multi-bin filters f1, f2, f1', f2' and i=1 . . . , the compliance factor $\rho_j(i)$ are used to determine the filtered output $g_{j,k}(i,l)$ according to Equation (8). The compliance factors $\rho$ and $\rho_2$ can be calculated from u(i,l) and z(i,l) as shown in FIGS. (6a), (6b), respectively. Therefore, $g_{j,k}(i,l)=f_j(i,l)$ and $g'_j(i,l)=f'_j(i,l)$ according to Equation (8). $\rho_j(i)$ can be written as $\rho_j(i) = num_j(i)/den_j(i)$. Then it is possible to solve for $num_j(i)$ and $den_j(i)$ using Equation (8) as shown in Equation (9).

$$num_j(i) = \sum_{l=1}^{NDL} (g^2_{j,k}(i,l) - g'^2_{j,k}(i,l)) \quad (9)$$

$$den_j(i) = \sum_{l=1}^{NDL} (g^2_{j,k}(i,l) + g'^2_{j,k}(i,l))$$

The first set of time-dependent variables or sampled data z(i,l) is used to calculate C(l,m). Finally, for computational purposes, the compliance factor $\rho_j(i)$ can be written as shown in equation (10).

$$\rho_j(i) = \frac{\sum_{k=i-(box_j+1)}^{k=i-1} num_j(k)}{1 + \sum_{k=i-(box_j+1)}^{i-1} den_j(k)} - 1 \quad (10)$$

where if $\Sigma\ num_j(i)<0$, then $\rho_j(i)=-\frac{1}{2}$, and if $\rho_j(i)-\rho_j(i-1)>$slew rate threshold, then $\rho_j(i)=\rho_j(i-1)+$slew rate threshold, where the slew rate threshold is a number corresponding to a maximum allowable slew rate.

The summations of $num_j$ and $den_j$ are performed over a window or box of sample indices i. Hence, the compliance factor $\rho_j(i)$ is computed using sums over windows or sets of sample points within Box1=8 samples of each other, or Box2=32 samples of each other yielding $num_j(i)$ and $den_j(i)$.

These sums are computed as rolling sums, adding leading window edge terms and subtracting trailing window edge terms. This means of summing is both efficient computationally and permits retention of a "dead band" bias in the form of specific initial values given to the initial numerator and denominator sums.

The size of the bias essentially limits the value of the smallest signal that can appear at the filter output. Hence, if a signal level is below a certain threshold level the output signal is zero.

Initial values for $num_j$ and $den_j$ are given on lines 123–127 of the source code. Here, the threshold level is set by initializing "denom[0]", "numer[0]" to 7200, −7200, respectively and "denom[1]", "numer[1]" to 26,400, −26, 000, respectively. Finally, the addition of "1" to the denominator window sum in Equation (10) is done merely to prevent division by zero in the event of a null input signal, i.e., z(i,l)=0 for all i=1 . . . NSMPL and l=1 . . . NLD.

Special features of the filter include: no assumption of stationary noise; compliance of leads used as well as compliance of sequences; dynamically varying passband; real-time capability; predictive of missing lead; limiting positive slew rate of compliance; positive coherence required; multi-band partitioning maintenance of diagnostic bandwidth; resolution of DC offset; integer arithmetic; deliberate deadband for subthreshold signals; and deadband for each band partition.

The present invention may thus be embodied in other specific forms without departing from the spirit or essential characteristics thereof. The presently disclosed embodiments are therefore to be considered in all respects as illustrative and not as restrictive, the scope of the invention being indicated by the appended claims rather than by the foregoing description, and all changes which come within the meaning and range of equivalency of the claims are therefore intended to be embraced therein.

While the description of the preferred embodiment of the present invention is directed to the area of electrocardiology, it should be understood that the present invention is also applicable to noise filtering used in other technical areas such as electroencephalography, sound amplification, data transmission and communications.

Oct 17 12:51 1990  patent.src Page 1

```
          ┌─────────────────────────────────────────────────────────┐
          │Prologue:                                                │
          │     C-language filter implementation for PC-ECG coprocessor
          │     card for IBM-compatible PCs                         │
          │                                                         │
     /*   │ filter.c */
     /*
          Copyright 1990
          Mortara Instrument, Inc
          Milwaukee, Wisconsin All rights reserved.
     */ include <memory.h> include "pcper.h"

define size(vec)  (sizeof(vec)>>1)

#define NULL    0
     #define SFAC    1                      /* 250 s/s circular buffer */
     #define LSF     0 define CIRCRAM 0x4000
     #define NLD     8                      /* Number of independent leads * extern int irqvec[8];                  /* interrupt vectors */
     extern char ram, ramend;
     extern struct zbuf {
             short zin[8];                  /* raw input data for each lead
             } zbuf[];                      /* input buffer with in & out po
     #define SMPL    size(zbuf[0])          /* Size in "short words" of zbuf
     #define NSMPL   (CIRCRAM/sizeof(zbuf[0]))   /* Total buffer samples define BOX1    8
     #define BOX2    32 define x(a)     zin[a-SMPL*(BOX2/2+64+1)]
     #define xp(a)    zin[a-SMPL*(BOX2/2+64+1+34)]
     #define x2(a)    zin[a-SMPL*(BOX2/2+64+1+68)]
     #define x2p(a)   zin[a-SMPL*(BOX2/2+64+1+76)]
     #define x8(a)    zin[a-SMPL*(BOX2/2+64+1+84)]
     #define x8p(a)   zin[a-SMPL*(BOX2/2+64+1+110)]
     #define f1(a)    zin[a-SMPL*(BOX2/2+64+1+136)]
     #define f1p(a)   zin[a-SMPL*(BOX2/2+64+1+149)]
     #define f2(a)    zin[a-SMPL*(BOX2/2+64+1+162)]
     #define f2p(a)   zin[a-SMPL*(BOX2/2+64+1+180)]
     #define f1out(a)        zin[a-SMPL*(BOX2/2+64+1+198-BOX1/2-1)]
     #define f2out(a)        zin[a-SMPL*(BOX2/2+64+1+199-BOX2/2-1+26)]
     #define xout(a)         zin[a-SMPL*(BOX2/2+64+1+240)]
```

Oct 17 12:51 1990  patent.src Page 2

```
53
54      long zbase[8];                          /* Baseline */
55      short rcvirq[8];                        /* interrupt counters */
56      unsigned char synch[3];                 /* irq data synchronization byte
57      struct zbuf *pzbi, *pzbo;               /* circular buffer in/out ptrs *
58
59      short fifo_ctr;                         /* Counter for FIFO interrupts *
60      short cvec[8], corr[49], coef[64];
61      int icorr[49], ivect[7];
62      int numer[2], denom[2];
63      struct numden
64              {
65              int n1 ,d1, n2, d2;
66              } numden[300], *pndmem;
67      short rho[2];
68      short ready;
69
70      extern int crystal;
71      unsigned char getcmd ();
72
73      /* ctrl */
74      #define CLKCL 0x80                      /* D7 - CLKCL, CLOCK OUTPUT CONTROL */
75      #define UART 0x20                       /* D5 - UART CONTROL */
76      #define N_RESET 0x10                    /* D4 - ~RESET */
77      #define TR_RC 0x8                       /* D3 - TR/RC TRANSMIT/RECEIVE CONTROL *
```

Oct 17 12:51 1990 patent.src Page 3

```
 78
 79    pcmain (parity, fault)
 80    {
 81    register short *pz, *py, cnt, sum, ld, res;
 82    register int isum, *icor, *ivec;
 83    register unsigned char *pc;
 84    short ldsol, ld2, c7[7];
 85
 86
 87
 88           |Initialization 1.
 89           |     Initial setting of variables
 90           |
 91           |
 92    memset (&ram, 0, &ramend - &ram - 0x100);
 93    memset (zbuf, 0, CIRCRAM);
 94
 95    pzbi = zbuf+NSMPL, pzbo = pzbi - 1;
 96
 97    amp.ctrl.byte1 = 0;
 98    amp.ctrl.byte2 = TR_RC;              /* set clock out  and in transmit mode *
 99    amp.ctrl.byte2 = TR_RC|N_RESET;      /* unreset ILGA */
100    amp.ctrl.byte2 = N_RESET;            /* enable receive */
101    amp.cnt.byte2 = 0;
102    amp.cnt.byte1 = 0;
103
104    synch[0] = 0x80;
105
106
107           |Initialization 2.
108           |     Await command bytes from PC (0x80 + ??)
109           |
110           |
111    while (getcmd () != 0x80) ;
112    amp.pcout.byte = parity, amp.pcout.byte = fault;
113
114    getcmd ();
115
116
117           |Initialization 3.
118           |     Initial filter parameters with deadband for 2
119           |     frequency bands
120           |
```

```
121    pndmem = numden+150;
122
123    denom[0] = 100 * 8 * (BOX1 + 1);
124    numer[0] = -denom[0] >> 3;
125
126    denom[1] = 100 * 8 * (BOX2 + 1);
127    numer[1] = -denom[1] >> 3;
128
129
130           | Initialization 4.
131           |     Allow interrupts from amplifier A/D subsystem
132           |     Wait > 10 seconds for system stabilization
133           |
```

Oct 17 12:51 1990  patent.src Page 4

```
134    setpri (0x2300);
135
136    while (rcvirq[4] < 250*10 || pzbi != zbuf+NSMPL+4) ;
137
138    setpri (0x2700);
```

Oct 17 12:51 1990  patent.src Page 5

```
139
140              Alternate Lead 1.
141                   Determine vector of coefficients for each lead which
142                   best predict given lead from all other leads
143
144     for (ldsol = 0; ldsol < NLD; ldsol++)
145             {
146
147              Alternate Lead 1.1
148                   Initialize correlation matrix and vector to zero
149
150
151         icor = icorr, ivec = ivect;
152         memset (icor, 0, 4*(NLD-1)*(NLD-1));
153         memset (ivec, 0, 4*(NLD-1));
154
155
156              Alternate Lead 1.2
157                   Accumulate correlation matrix and vector elements from
158                   sample-to-sample difference products over ~1000 terms
159
160         for (ld2 = 0; ld2 < NLD; ld2++)
161                 {
162                 if (ld2 == ldsol) continue;
163                 for (ld = 0; ld <= ld2; ld++)
164                         {
165                         if (ld == ldsol) continue;
166                         py = zbuf[8].zin+ld, pz = zbuf[8].zin+ld2;
167                         for (cnt = 8, isum = 0; cnt < NSMPL-4; cnt++)
168                                 {
169                                 sum = *py - *(py-SMPL);
```

```
170                             res = *pz - *(pz-SMPL);
171                             isum += sum * res;
172                             py += SMPL, pz += SMPL;
173                             }
174                     *icor++ = isum;
175                     }
176             icor += NLD - ld;
177             if (ld <= ldsol) icor--;
178             py = zbuf[8].zin+ldsol, pz = zbuf[8].zin+ld2;
179             for (cnt = 8, isum = 0; cnt < NSMPL-4; cnt++)
180                     {
181                     sum = *py - *(py-SMPL);
182                     res = *pz - *(pz-SMPL);
183                     isum += sum * res;
184                     py += SMPL, pz += SMPL;
185                     }
186             *ivec++ = isum;
187             }
188
189
190     |Alternate Lead 1.3
191     |       Find trace of correlation matrix (/64)
192     |
193     |
194     for (ld = 0, isum = 0; ld < NLD*(NLD-1); ld += NLD)
```

Oct 17 12:51 1990  patent.src Page 6

```
195                     isum += icorr[ld] >> 6;
196             sum = isum >> 16;
```

```
                                                    Oct 17 12:51 1990  patent.src Page 7

197
198            |Alternate Lead 1.4
199            |        Determine shift normalization to keep trace < 16384
200            |
201            |
202            if (sum >= 0) for (res = 8; sum != 0; sum >>= 1) res++;
203            else res = 24;
204
205
206            |Alternate Lead 1.5
207            |        Scale matrix and vector to permit accurate matrix
208            |        inversion
209            |
210            for (pz = corr, icor = icorr, cnt = 49; --cnt >= 0; )
211                    *pz++ = *icor++ >> res;
212            for (pz = cvec, ivec = ivect, cnt = 7; --cnt >= 0; )
213                    *pz++ = *ivec++ >> res;
214
215
```

```
216         Alternate Lead 1.6
217              Symmetrize matrix and add diagonal degeneracy
218              prevention terms
219
220         sum = isum >> (res+2), cnt = sum << 1;
221
222         for (ld2 = 0; ld2 < NLD-1; ld2++)
223                 {
224                 for (ld = ld2+1; ld < NLD-1; ld++)
225                         corr[(NLD-1)*ld2+ld] = corr[(NLD-1)*ld+ld2];
226
227                 corr[NLD*ld2] += cnt;
228                 }
229
230
231         Alternate Lead 1.7
232              Find solution vector "c7" and save in "coef" matrix
233              Note that "coef" is scaled up by 256 for accuracy of
234              subsequent integer arithmetic
235              Put diagonal of 8x8 coef matrix to -1 (-256) so that
236              application of coef to vector of leads yields the
237              difference of lead and its predicted value
238
239         matrix (NLD-1, corr, cvec, c7);
240         memcpy (coef+64+16*ldsol, cvec, 14);
241
242         pz = &coef[8*ldsol];
243         *(pz+ldsol) = -256;
244
245         memcpy (pz, c7, 2*ldsol);
246         memcpy (pz+ldsol+1, c7+ldsol, 2*(7-ldsol));
247         }
```

```
248         Alternate Lead 2.
249              Re-initialize variables, re-synchronize with interrupts,
250              signal interrupt subroutine that coefficient matrix is
251              ready
252
253
254         memset (zbuf, 0, CIRCRAM), rcvirq[4] = 0, rcvirq[3] = 0;
255         pzbi = zbuf+NSMPL, pzbo = pzbi - 1;
256         synch[0] = 0x80, fifo_ctr = 0;
257
258         while (!(amp.ctrl.byte1 & 0x10))         /* As long as FIFO is not empty
259                 if (amp.fifo.byte) ;
260
```

```
261    ready = 1;
262    setpri (0x2300);
263
264    while (1) ;
265    }
```

Oct 17 12:51 1990   patent.src Page 9

```
266
267         /*─────────────────────────────────────────
268         | Function getcmd ()
269         |       Receive command bytes from host PC
270         |─────────────────────────────────────────
271    unsigned char getcmd ()
272    {
```

```
273    register unsigned char xx;
274
275
276    while (amp.ctrl.byte1 & 0x40) ;           /* Wait for byte in input latch
277
278    xx = amp.pcin.byte;
279    if (xx == 'X') setpri (0x2700), load ();
280    amp.pcout.byte = xx;                      /* Echo */
281    return xx;
282    }
```

283

```
284
285             |Interrupt Function ampirq ()
286             |       Accept amplifier & A/D subsystem interrupts at 1
287             |       millisecond intervals
288             |
289     ampirq ()
290     {
291     register unsigned char *pa, *pc;
292     register short error, shift;
293     register short cnt, cnt4;
294
295
296
297             |Interrupt 1.
298             |       Amplifier-A/D system interrupts with 18 byte data frame
299             |       in FIFO at amp.fifo.byte.  Frame consists of "synch"
300             |       byte plus 16 data bytes (8 leads x 2 bytes) plus status
301             |       byte (unused in this application).  Synch plus 8 bytes
302             |       are already read into address "pzbi" by pre-interrupt
303             |       function
304             |
305     pa = &.fifo.byte;
306     pc = (unsigned char *) pzbi, pc += 8;
307
308
309             |Interrupt 2.
310             |       Read remaining 8 frame data bytes and discard status.
311             |       Set next expected synch byte.
312             |
313     for (cnt = NLD; --cnt >= 0; ) *pc++ = *pa;
314     if (*pa == 0) ;                                 /* Extra read to empty F
315
316     synch[0] = (synch[0] + 1) & 0x83;
317
318
319             |Interrupt 3.
320             |       Maintain "pzbi" as circular buffer pointer.
321
322             |
323     if (pc > ((unsigned char *) zbuf) + 2*CIRCRAM - sizeof (zbuf[0]))
324             pc -= CIRCRAM;
325     pzbi = (struct zbuf *) pc;
326
327
328             |Interrupt 4.
329             |       Count 1ms interrupts, and average groups of 4 to net
330             |       1 sample each 4ms.
331             |
332     .fifo_ctr++;
333     if (!(fifo_ctr & 4)) return;
334     fifo_ctr = 0;
335     pc -= 3 * sizeof (zbuf[0]);
336     pzbi = (struct zbuf *) pc;
337
338     #define pz1     ((short *) pc)
```

Oct 17 12:51 1990   patent.src  Page 11

```
339    #define pz2      ((short *) pa)
340
341    pz1 -= SMPL;
342    for (cnt = NLD; --cnt >= 0; )
343            {
344            for (cnt4 = 4, error = 0, pz2 = pz1; --cnt4 >= 0; pz2 += SMPL)
345                    shift = *pz2, shift >>= 2, error += shift;
346            *pz1++ = error;
347            }
348
349    irq250 ();
350    return;
351    }
```

Oct 17 12:51 1990  patent.src Page 12

```
352
353              |Interrupt Function irq250 ()
354              |         Perform 250 sample/second filter functions
355              |
356              |
357      irq250 ()
358      {
359      register unsigned char *pa;
360      register short *pz, *pzold;
361      register struct numden *pnd;
362      register short error, shift;
363      register unsigned long offset;
364      register int cnt, isum;
365      short ndx;
366
367      #define ps      ((struct zbuf *) pz)
368      #define psold   ((struct zbuf *) pzold)
369      #define px      ((short *) pa)
370
371
372      rcvirq[4]++;
373      setpri (0x2300);
374
375
376              |Baseline Filter 1.
377              |         Remove low frequency components of input by applying
378              |         single-pole high pass filter with 4.096s time constant.
379              |
380      pz = (short *) pzbo, pzold = pz + NLD;
381      for ((long *) pa = zbase; pz < pzold; )
382              {
383              error = *pz, error -= *(short *) pa;    /* error is mis-nomer */
384              if (error > 0x7F00)
385                      *(short *) pa += error, error = 0;     /* Reset baselin
386              *pz++ = error;
387              *((long *) pa)++ += error << (6-LSF);
388              }
389
390
391      pz -= NLD, pzold = pz;
392      if (!ready) return;
```

Oct 17 12:51 1990   patent.src Page 13

```
393
394
395⸴           | Filter 1.
396           |       Maintain circular buffer pointer to numerator and
397           |       denominator terms
398           |
399     pnd = pndmem, pnd++;
400     if (pnd >= numden+300) pnd -= 150;
401     pndmem = pnd;
402
403
404           | Filter 2.
405           |       For each lead:
406
407           |
408                                       /* Estimate 284 * 8 memory cycles */
409     for (px = coef, cnt = NLD; --cnt >= 0; pz++, pzold -= NLD)
410         (
411
412           | Filter 2.1
413           |       Calculate:
414           |               xp(0) as "sample - predicted sample" value
415           |               x(0) as "sample + predicted sample" value
416           |
417           |               x2(0) as pair average of x(0)
418           |               x2p(0) as pair average of xp(0)
419           |               x8(0) as 8-pt average of x(0)
420           |               x8p(0) as 8-pt average of xp(0)
421           |
422         for (shift = NLD, isum = 0; --shift >= 0; pzold++)
423                 isum += psold->zin[0] * *px++;
424
425         isum >>= 8, error = isum, ps->xp(0) = error;
426         shift = ps->zin[0], shift <<= 1, shift += error, ps->x(0) = shif
427
428         shift += (ps-1)->x(0);
429         shift >>= 1, ps->x2(0) = shift;
430         shift += (ps-2)->x2(0), shift += (ps-4)->x2(0);
431         shift += (ps-6)->x2(0);
432         shift >>= 2, ps->x8(0) = shift;
433
434         error += (ps-1)->xp(0);
435         error >>= 1, ps->x2p(0) = error;
```

```
436             error += (ps-2)->x2p(0), error += (ps-4)->x2p(0);
437             error += (ps-6)->x2p(0);
438             error >>= 2, ps->x8p(0) = error;
439             }
```

Oct 17 12:51 1990  patent.src Page 14

```
440        _____
441       |Filter 3.
442       |       Initialize numerator/denominator sums to zero
443       |       For each lead:
444        _____
445    cnt = 0, offset = 0;
446    for (ndx = NLD, pz = pzold; --ndx >= 0; pz++)    /* Estimate 133 * 8 cycl
447            {
448        _____
449       |Filter 3.1
450       |       Calculate frequency band 1 filter output minus input
451       |       for filter term first calculated "BOX1/2+1" sample
452       |       intervals ago
453        _____
454    error = (ps-BOX1/2-1)->f1(0), error -= (ps-BOX1/2-1)->f1p(0);
455    (ps-BOX1/2-1)->f1out(0) = (error * rho[0]) >> 16;
456
457        _____
458       |Filter 3.2
459       |       Calculate band 1 filter output of x(0), and add squared
460       |       output to numerator and denominator terms
461        _____
462    error = (ps-2)->x2(0), error += (ps-5)->x2(0), shift = error;
463    error -= ps->x2(0), error -= (ps-7)->x2(0), error >>= 2;
464    error += shift, error >>= 1, error -= (ps-4)->x(0);
465    ps->f1(0) = error;
466    isum = error * error;
467    cnt += isum, offset += isum;
468
469
470        _____
471       |Filter 3.3
472       |       Calculate band 1 filter output of xp(0), and subtract/
473       |       add squared result to numerator/denominator terms
        _____
474    error = (ps-2)->x2p(0), error += (ps-5)->x2p(0), shift = error;
475    error -= ps->x2p(0), error -= (ps-7)->x2p(0), error >>= 2;
476    error += shift, error >>= 1, error -= (ps-4)->xp(0);
```

```
477            ps->flp(0) = error;
478            isum = error * error;
479            cnt -= isum, offset += isum;
480            }
```

Oct 17 12:51 1990  patent.src Page 15

```
481
482         |Filter 4.
483         |       Calculate rho1 = (ratio-1)/2 of average of last "BOX1+1"
484         |       numerator and denominator terms of band 1
485         |
486                                 /* Estimate 128 memory cycles */
487    pnd->n1 = cnt, (pnd-150)->n1 = cnt, pnd->d1 = offset, (pnd-150)->d1 = of
488    cnt -= (pnd-BOX1-1)->n1,            offset -= (pnd-BOX1-1)->d1;
489    cnt += numer[0],                    offset += denom[0];
490    denom[0] = offset;
491
492
493         |Filter 4.1
494         |       For average numerators <= 0, assign rho1 = -1/2
495         |
496
497    if ((numer[0] = cnt) <= 0) rho[0] = -0x8000;
498    else    (
499
500         |Filter 4.2
501         |       For average numerators > 0, calculate "rho1" after
502         |       normalizing average numerator & denominator and
503         |       protecting against null denominator by adding 1.
504
505    offset >>= 1, shift = offset >> 16;
506    while (shift != 0) offset >>= 2, cnt >>= 2, shift >>= 2;
507    offset++, cnt >>= 2;
508
509    error = (unsigned int)(cnt << 16) / (unsigned short) offset;
510    error -= 0x8000;
511
```

```
512        |Filter 4.3
513        |       Positive rate of increase of rho1 is limited
514        |
515        |
516         shift = rho[0], shift += 32000/BOX1;
517         if (error > shift) rho[0] = shift;       else rho[0] = error;
518         }
```

Oct 17 12:51 1990   patent.src Page 16

```
519
520        |Filter 5.
521        |       Initialize numerator/denominator sums to zero
522        |       For each lead:
523        |
524    cnt = 0, offset = 0;
525    for (ndx = NLD, pz = pzold; --ndx >= 0; pz++)    /* Estimate 132 * 8 cycl
526        {
527
528        |Filter 5.1
529        |       Calculate frequency band 2 filter output minus input
530        |       for filter term first calculated "BOX2/2+1" sample
531        |       intervals ago
532
533         error = (ps-BOX2/2-1)->f2(0), error -= (ps-BOX2/2-1)->f2p(0);
534         (ps-BOX2/2-1)->f2out(0) = (error * rho[1]) >> 16;
535
536
537        |Filter 5.2
538        |       Calculate band 2 filter output of x(0), and add squared
539        |       output to numerator and denominator terms
540
541         error = (ps-8)->x8(0), error += (ps-17)->x8(0), shift = error;
542         error -= ps->x8(0), error -= (ps-25)->x8(0), error *= 3, error >
543         error += shift, error >>= 1, error -= (ps-16)->x(0);
```

```
544         error -= (ps-(BOX2-BOX1)/2)->f1(0), ps->f2(0) = error;
545         isum = error * error;
546         cnt += isum, offset += isum;
547
548         ┌─────────────────────────────────────────────────────────────
549         │Filter 5.3
550         │       Calculate band 2 filter output of xp(0), and subtract/
551         │       add squared result to numerator/denominator terms
552         ├─────────────────────────────────────────────────────────────
553         error = (ps-8)->x8p(0), error += (ps-17)->x8p(0), shift = error;
554         error -= ps->x8p(0), error -= (ps-25)->x8p(0), error *= 3, error
555         error += shift, error >>= 1, error -= (ps-16)->xp(0);
556         error -= (ps-(BOX2-BOX1)/2)->f1p(0), ps->f2p(0) = error;
557         isum = error * error;
558         cnt -= isum, offset += isum;
559     }
```

Oct 17 12:51 1990  patent.src Page 17

```
560
561         ┌─────────────────────────────────────────────────────────────
562         │Filter 6.
563         │       Calculate rho2 = (ratio-1)/2 of average of last "BOX2+1"
564         │       numerator and denominator terms of band 2
565         ├─────────────────────────────────────────────────────────────
                                              /* Estimate 129 memory cycles */
566     pnd->n2 = cnt, (pnd-150)->n2 = cnt, pnd->d2 = offset, (pnd-150)->d2 = of
567     cnt -= (pnd-BOX2-1)->n2,             offset -= (pnd-BOX2-1)->d2;
568     cnt += numer[1],                     offset += denom[1];
569     denom[1] = offset;
570
571
572         ┌─────────────────────────────────────────────────────────────
573         │Filter 6.1
574         │       For average numerators <= 0, assign rho2 = -1/2
575         ├─────────────────────────────────────────────────────────────
576     if ((numer[1] = cnt) <= 0) rho[1] = -0x8000;
577     else    {
578
```

```
579       Filter 6.2
580            For average numerators > 0, calculate "rho2" after
581            normalizing average numerator & denominator and
582            protecting against null denominator by adding 1.
583
584       offset >>= 1, shift = offset >> 16;
585       while (shift != 0) offset >>= 2, cnt >>= 2, shift >>= 2;
586       offset++, cnt >>= 2;
587
588       error = (unsigned int)(cnt << 16) / (unsigned short) offset;
589       error -= 0x8000;
590
591       Filter 6.3
592            Positive rate of increase of rho2 is limited
593
594
595       shift = rho[1], shift += 32000/BOX2;
596       if (error > shift) rho[1] = shift;      else rho[1] = error;
597       )
```

```
598
599       Filter 7.
600            For each lead, calculate output xout(0) as original
601            input zin[0] less corrections from band 1 and 2 filters
602
603                                          /* Estimate 16 * 8 memory cycles
604   for (cnt = NLD, pz = pzold; --cnt >= 0; pz++)
605       {
606       error = (ps-16-BOX2/2-1)->zin[0];
607       error -= (ps-16-BOX2/2-1+16)->f2out(0);
608       error -= (ps-16-BOX2/2-1+4)->flout(0);
609       ps->xout(0) = error;
610       )
```

611    pz = pzold;

612
613    no_filt:
614
615    #define pc      ((unsigned char *) pzold)
616
617
618            |Filter 8.

```
619                   Maintain circular buffer pointer "pzbo"
620
621
622   if ((char *) pz >= ((char *) zbuf) + 2*CIRCRAM - 2*sizeof (zbuf[0]))
623         (char *) pz -= CIRCRAM;
624   pzbo = (struct zbuf *) pz + 1;
625
626
627                  Filter 9.
628                         Deliver filtered output xout(0) to PC host and
629                         signal interrupt to PC
630
631   pa = &.pcout.byte;
632   *pa = 0x80;                                    /* Synch byte          */
633   pc = (unsigned char *) &ps->xout(0);
634   for (cnt = NLD; --cnt >= 0; ) *pa = *pc++; *pa = *pc++;
635
636   *pa = 0, *pa = 0;
637
638   amp.pcin.byte = (char ) cnt;                   /* Flash interrupt */
639   return;
640   }
641
```

I claim:

1. A method for providing an output signal corresponding to a signal produced by a signal source, the signal produced by the signal source having a series of repetitious, generally similar features, said method reducing the presence of noise in the provided output signal and comprising the steps of:

sequentially sensing a plurality of said repetitious signal features to obtain a plurality of received signals in which noise may be present, each of said plurality of received signals corresponding to one of said repetitious signal features;

forming at least one set of determination points in the plurality of received signals;

measuring the actual magnitude of said received signals at the determination points;

selecting a given one of the received signal as that for which a corresponding output signal having reduced noise will be produced;

generating, from the actual magnitudes of the received signals other than the given received signal, an estimated signal representing an estimated magnitude of the given received signal for at least one determination point in the given received signal;

comparing the given received signal and the estimated signal on the basis of their magnitudinal properties;

generating a compliance signal from said comparison of the given received signal and estimated signal indicative of the compliance between the signals, differences in the given received signal and estimated signal being attributable to noise in the given received signal; and generating, from the given received signal and the compliance signal, said output signal in which the presence of noise is reduced.

2. The method according to claim 1 wherein the step of generating an estimated signal is further defined as generating an estimated signal having a magnitude that minimizes the difference between the magnitude of the estimated signal and the actual signal magnitudes of the received signals other than the given received signal.

3. The method according to claim 2 wherein the step of generating an estimated signal is further defined as generating an estimated signal, the magnitude of which produces the least squared error with respect to the actual magnitudes of the received signals other than the given received signal.

4. The method according to claim 1 wherein the step of forming at least one set of determination points in the plurality of received signals is further defined as forming a plurality of sets of determination points in the plurality of received signals and wherein the step of generating an estimated signal is further defined as generating an estimated signal representing the estimated magnitude of the given received signal for a selected plurality of determination points in the given received signal.

5. The method according to claim 1 wherein the comparing step is further defined as comparing the given received signal and the estimated signal at at least one determination point in the given received signal.

6. The method according to claim 1 wherein the step of generating said output signal is further defined as altering the magnitude of the given received signal in accordance with the compliance signal.

7. The method according to claim 6 wherein the step of generating said output signal is further defined as attenuating the given received signal in accordance with the compliance signal.

8. A method according to claim 1 wherein the step of generating the estimated signal is further defined as generating an estimated signal for a plurality of determination points in the given received signal; the step of generating a compliance signal is further defined as providing the compliance for each determination point in a range of said determination points and generating a compliance signal for a given determination point in said range from the compliance for each determination point in the range; and the step of generating said output signal is further defined as generating said output signal from the given received signal at the given determination point and the so-generated compliance signal.

9. The method according to claim 8 further defined as generating said output signal from the given received signal at a determination point in the center of said range of determination points.

10. The method according to claim 1 wherein the plurality of received signals include feature segments of distinguishable magnitudinal variation and wherein the step of generating the estimated signal is further defined as generating an estimated signal from the actual magnitudes of the received signals other than the given received signal in the feature segments of distinguishable magnitudinal variation.

11. A method for producing an EKG output signal indicative of electrical phenomena exhibited by a patient's heart, the phenomena including a series of repetitious, generally similar, electrical signal features associated with the functioning of the heart, said method reducing the presence of noise in the produced EKG output signal so that the EKG output signal is an accurate indication of the heart phenomena, said method comprising the steps of:

sequentially sensing a plurality of said repetitious signal features;

obtaining, from the sensing, a plurality of received EKG signals in which noise may be present, each of said plurality of received EKG signals corresponding to one of said repetitious signal features;

forming at least one set of common determination points in the plurality of received EKG signals;

measuring the actual magnitude of said received EKG signals at the determination points;

selecting a given one of the received EKG signal as that for which a corresponding EKG output signal having reduced noise will be produced;

generating, from the actual magnitudes of the received EKG signals other than the given received EKG signal, an estimated EKG signal representing an estimated magnitude of the given received EKG signal for at least one determination point in the given received EKG signal;

comparing the given received EKG signal and the estimated EKG signal on the basis of their magnitudinal properties;

generating a compliance signal from said comparison of the given received EKG signal and estimated EKG signal indicative of the compliance between the signals, differences in the given received EKG signal and estimated EKG signal being attributable to noise in the given received EKG signal; and generating, from the given received EKG signal and the compliance signal, said EKG output signal having reduced noise.

12. The method according to claim 11 wherein the step of generating an estimated EKG signal is further defined as generating an estimated EKG signal having a magnitude that minimizes the difference between the magnitude of the estimated EKG signal and the actual signal magnitudes of the received EKG signals other than the given received EKG signal.

13. The method according to claim 12 wherein the step of generating an estimated EKG signal is further defined as generating an estimated EKG signal, the magnitude of which produces the least squared error with respect to the actual magnitudes of the received EKG signals other than the given received EKG signal.

14. The method according to claim 11 wherein the step of forming at least one set of determination points in the plurality of received EKG signals is further defined as forming a plurality of sets of determination points in the plurality of received EKG signals and wherein the step of generating an estimated EKG signal is further defined as generating an estimated EKG signal representing the estimated magnitude of the given received EKG signal for a selected plurality of determination points in the given received EKG signal.

15. The method according to claim 11 wherein the comparing step is further defined as comparing the given received EKG signal and the estimated EKG signal at at least one determination point in the given received EKG signal.

16. The method according to claim 11 wherein the step of generating said EKG output signal is further defined as altering the magnitude of the given received EKG signal in accordance with the compliance signal.

17. The method according to claim 16 wherein the step of generating said EKG output signal is further defined as attenuating the given received signal in accordance with the;compliance signal.

18. A method according to claim 11 wherein the step of generating the estimated EKG signal is further defined as generating an estimated EKG signal for a plurality of determination points in the given received signal; the step of generating a compliance signal is further defined as providing the compliance for each determination point in a range of said determination points and generating a compliance signal for a given determination point in said range from the compliance for each determination point in the range; and the step of generating said EKG output signal is further defined as generating said EKG output signal from the given received EKG signal at the given determination point and the so-generated compliance signal.

19. The method according to claim 18 further defined as generating said EKG output signal from the given received EKG signal at a determination point in the center of said range of determination points.

20. The method according to claim 11 wherein the plurality of received EKG signals include feature segments of distinguishable magnitudinal variation and wherein the step of generating the estimated EKG signal is further defined as generating an estimated EKG signal from the actual magnitudes of the received EKG signals other than the given received EKG signal in the feature segments of distinguishable magnitudinal variation.

21. The method according to claim 20 wherein the plurality of received EKG signals include QRS feature segments and wherein the estimated EKG signal is generated from signal magnitudes in the QRS feature segments.

22. Signal processing apparatus for providing an output signal corresponding to a signal produced by a signal source, the signal produced by the signal source having a series of repetitious, generally similar features, said apparatus reducing the presence of noise in the provided output signal, said apparatus being suitable for use with sensor means for obtaining the signal produced by the signal source, in which signal noise may be present, said apparatus comprising:

an input receiving the signal obtained by the sensor means and forming a plurality of input signals each of which corresponds to one of the repetitious signal features;

means forming at least one set of determination points in said plurality of input signals;

a measurement circuit measuring the actual magnitude of said plurality of input signals at the determination points in the plurality of input signals;

a selector selecting a given one of said input signal as that for which a corresponding output signal having reduced noise will be produced;

an estimated magnitude signal generator for generating, from the actual magnitudes of the input signals other than the selected input signal, an estimated signal representing an estimated magnitude of the selected input signal for at least one determination point in the selected input signal;

a comparator comparing the selected input signal and the estimated signal on the basis of their magnitudinal properties and determining the compliance between the selected input signal and the estimated signal, differences in the selected input signal and estimated signal being attributable to noise in the selected input signal; and a signal generator generating, from the selected input signal and the compliance, said output signal in which noise is reduced.

23. The signal processing apparatus according to claim 22 wherein said estimated magnitude signal generator is further defined as generating an estimated signal having a magnitude that minimizes the difference between the magnitude of the estimated signal and the actual magnitudes of the input signals other than the selected input signal.

24. The signal processing apparatus according to claim 23 wherein said estimated magnitude signal generator is further defined as generating an estimated signal, the magnitude of which produces the least squared error with respect to the actual magnitudes of the input signals other than the selected input signal.

25. The signal processing apparatus according to claim 23 wherein said forming means is further defined as forming a plurality of sets of determination points in said plurality of input signals and wherein the estimated magnitude signal generator is further defined as generating an estimated signal for a selected plurality of determination points.

26. The signal processing apparatus according to claim 22 wherein said comparator is further defined as comparing the selected input signal and the estimated signal at determination points in the selected input signal.

27. The signal processing apparatus according to claim 22 wherein the signal generator is further defined as altering the selected input signal in accordance with the compliance to generate said output signal.

28. The signal processing apparatus according to claim 27 wherein said signal generator is further defined as attenuating the selected input signal in accordance with the compliance to generate said output signal.

29. The signal processing apparatus according to claim 22 wherein said estimated magnitude signal generator is further defined as generating an estimated signal for a plurality of determination points in said selected input signal; wherein said comparator is further defined as determining the compliance for each determination point in a range of said determination points and for providing a compliance for a given determination point in said range from the compliance for each determination point in the range; and wherein said signal generator is further defined as generating said output signal at a determination point in said range of determination points in accordance with the so-determined compliance.

30. The signal processing apparatus according to claim 29 wherein said signal generator is further defined as generating said output signal at a determination point in the center of said range of determination points.

31. Signal processing apparatus for producing an EKG output signal indicative of electrical phenomena exhibited by a patient's heart, the phenomena including a series of repetitious, generally similar, electrical signal features associated with the functioning of the heart, said apparatus reducing the presence of noise in the produced EKG output signal so that the EKG output signal is an accurate indication of the heart phenomena, said apparatus being suitable for use with sensor means for obtaining an EKG signal in which noise may be present, said apparatus comprising:

an input receiving the EKG signal obtained by the sensor means and forming a plurality of input signals, each of which corresponds to one of the repetitious signal features;

means forming at least one set of determination points in said plurality of input signals;

a measurement circuit measuring the actual magnitude of said plurality of input signals at the determination points in the plurality of input signals;

a selector selecting a given one of said input signal as that for which a corresponding EKG output signal having reduced noise will be produced;

an estimated magnitude signal generator for generating, from the actual magnitudes of the input signals other than the selected input signal, an estimated signal representing an estimated magnitude of the selected input signal for at least one determination point in the selected input signal;

a comparator comparing the selected input signal and the estimated signal on the basis of their magnitudinal properties and determining the compliance between the selected input signal and the estimated signal, differences in the selected input signal and estimated signals being attributable to noise in the selected input signal; and a signal generator generating, from the selected input signal and the compliance, said EKG output signal in which noise is reduced.

32. The signal processing apparatus according to claim 31 wherein said estimated magnitude signal generator is further defined as generating an estimated signal having a magnitude that minimizes the difference between the magnitude of the estimated signal and the actual magnitudes of the obtained input signals other than the selected input signal.

33. The signal processing apparatus according to claim 32 wherein said estimated magnitude signal generator is further defined as generating an estimated signal, the magnitude of which produces the least squared error with respect to the actual magnitudes of the input signals other than the selected input signal.

34. The signal processing apparatus according to claim 31 wherein said forming means is further defined as forming a plurality of sets of common determination points in said plurality of input signals and wherein the estimated magnitude signal generator is further defined as generating an estimated signal over a selected plurality of determination points.

35. The signal processing apparatus according to claim 31 wherein said comparator is further defined as comparing the selected input signal and the estimated signal at determination points in the selected input signal.

36. The signal processing apparatus according to claim 31 wherein the signal generator is further defined as altering the selected input signal in accordance with the compliance to generate said output signal.

37. The signal processing apparatus according to claim 36 wherein said signal generator is further defined as attenuating the selected input signal in accordance with the compliance to generate said output signal.

38. The signal processing apparatus according to claim 31 wherein said estimated magnitude signal generator is further defined as generating an estimated signal for a plurality of determination points in said selected input signal; wherein said comparator is further defined as determining the compliance for each determination point in a range of said determination points and for providing a compliance for a given determination point in said range from the compliance for each determination point in the range; and wherein said signal generator is further defined as generating said output signal at a determination point in said range of determination points in accordance with the so determined compliance.

39. The signal processing apparatus according to claim 38 wherein said signal generator is further defined as generating said output signal at a determination point in the center of said range of determination points.

* * * * *

UNITED STATES PATENT AND TRADEMARK OFFICE
CERTIFICATE OF CORRECTION

PATENT NO. : 5,490,515
DATED : February 13, 1996
INVENTOR(S) : Mortara

It is certified that error appears in the above-indentified patent and that said Letters Patent is hereby corrected as shown below:

On title page, item
[75] Inventor:     Delete "avid" and substitute therefor "David"

[56] References Cited
U.S. PATENT DOCUMENTS 4,779,617     10/1988     Whigham

The correct date is "10/1975"

CLAIM 17, Col. 57, line 4, delete the semicolon after the word "the"

Signed and Sealed this

Eighteenth Day of June, 1996

Attest:

BRUCE LEHMAN

Attesting Officer        Commissioner of Patents and Trademarks